United States Patent [19]

Bourgois et al.

[11] Patent Number: 4,670,543

[45] Date of Patent: Jun. 2, 1987

[54] PROCESS FOR OBTAINING COMPLEX FVIII/VWF OF THERAPEUTICAL USE AND RESULTING PRODUCTS

[75] Inventors: Alain Bourgois; Marylène Delezay, both of Marseilles; Vincent Fert, Nyons, all of France

[73] Assignee: Immunotech, Marseilles, France

[21] Appl. No.: 777,335

[22] Filed: Sep. 18, 1985

[30] Foreign Application Priority Data

Sep. 18, 1984 [FR] France .................................. 8414480

[51] Int. Cl.$^4$ ................................................ C07G 7/00
[52] U.S. Cl. ....................................... 530/383; 424/85; 424/101; 514/2; 514/802; 514/834; 436/548; 525/54.1
[58] Field of Search ........................ 260/112 B, 112 R; 525/54.1; 424/101, 85; 514/2, 802, 834; 436/548; 530/383

[56] References Cited

U.S. PATENT DOCUMENTS 4,361,509  12/1982  Zimmerman et al. .............. 530/383

OTHER PUBLICATIONS

Chemical Abstracts, vol. 96, No. 19, May 10, 1982, p. 571, No. 160565y, Columbus, Ohio, US; D. N. Fass et al.: "Monoclonal Antibodies to Porcine Factor VIII Coagulant and Their Use in the Isolation of Active Coagulant Protein".

Biological Abstracts, vol. 78, No. 8, 1984, Philadelphia, Pa., H. V. Stel et al; "Characterization of 25 Monoclonal Antibodies to Factor VIII-von Willebrand Factor: Relationship Between Ristocetin—Induced Platelet Aggregation and Platelet Adherence to Subendothelium": Blood 63(6): 1408–1415, 1984.

Chem. Abstracts, vol. 103, No. 5, p. 376, 1985, Columbus, Ohio, P. Avner et al. "Monoclonal Anitbodies Against the Human Factor VIII von Willebrand Molecule: Characterization and Potential for Screening of von Willebrand Patients" Dev.Biol.Stand. 1984.

*Primary Examiner*—John Kight
*Assistant Examiner*—Nathan M. Nutter

[57] ABSTRACT

The invention relates to a process for producing FVIII/vWF complexes for therapeutical use possessing both haemophilic A activity and Willebrand activity as well as a high degree of purity, such process substantially comprising the steps of fixing the FVIII/vWF complex in physiological conditions on a particular monoclonal antibody and releasing said complex by means of a suitable elution medium having no effect on the functions of the FVIII/vWF complex but able to dissociate the bonds linking the selected monoclonal anitbody to the FVIII/vWF complex, then collecting the latter in a highly purified form.

12 Claims, No Drawings

PROCESS FOR OBTAINING COMPLEX FVIII/VWF OF THERAPEUTICAL USE AND RESULTING PRODUCTS

This invention relates to the production of the FVIII/vWF complex for therapeutical use possessing both the antihaemophilic A activity and Willebrand activity as well as a high degree of purity.

Several processes for purification of the antihaemophilic factor A with a view to therapeutically using such factor have already been described; they refer to various methods such as cryoprecipitation, selective precipitation, adsorption and fractionated elution and ion exchange chromatography.

It is known that antihaemophilic A activity is carried by the factor VIII (designated FVIII or VIII:C) which in the physiological state is associated with Willebrand factor (designated vWF or VIIIR:Ag) in form of the complex FVIII/wWF.

The main forms of antihaemophilic factor A for therapeutical use which are most generally known and commercialized comprise:
  either the cryoprecipitate which is obtained by thawing of the fresh blood plasma at 4° C.;
  or the concentrate which is obtained from the cryoprecipitate after two polyethyleneglycol precipitation steps.

With regard to both of these forms it is noted that the concentration of cryoprecipitate (which is very contaminated with fibrinogen) is of 5 to 10 international units (I.U.) per ml, while a value of 25 I.U. per ml can be obtained for the concentrate.

With regard to the concentrate, it is to be noted however, that during its preparation a major portion of the von Willebrand factor was lost so that the concentrate cannot be efficiently used for restoring the deficiency of subjects having von Willebrand disease.

Moreover, although it is obtained under a purer form than the cryoprecipitate, the concentrate possesses the disadvantage of being still strongly contaminated; the complex constitutes less than 10% of the total proteins of the concentrate.

Original solutions permitting to obtain a factor VIII of high purity have already been proposed. Such solutions are generally based on the principle of fixing the FVIII/wWF complex (of blood origin) on a solid carrier, washing the contaminating molecules, then eluting the procoagulant factor VIII (FVIII:C) in isolated form by dissociation of the complex using a saline buffer of high ionic force (NaCl 1M or Cacl$_2$, 0.25 to 0.5M). The initial complex is usually fixed to said solid carrier either by polyclonal antibodies (E. G. D. Tuddenham et al. Journal of Laboratory Clinical Medicine (1979), vol. 93, page 10) or monoclonal antibodies (T. S. Zimmermann and C. A. Fulcher, United States patent (1982) No 4 361 509) which are coupled to "Sepharose" gel beads or by means of a suitable ion exchange resin such as aminohexyl-Sepharose (D. E. G. Austen, British Journal of Haematology (1979), vol. 43, page 669).

However, it ought to be noticed that during the elution the linkage of the von Willebrand factor to the solid phase is not broken and that for this reason the product obtained by these different processes consists of procoagulant factor VIII (FVIII:C) alone, therefore not containing said von Willebrand factor (vWF or VIIIR:Ag), such factor being required for people having Willebrand disease and that moreover such factor VIII isolated in this manner is not under its physiological form (which is normally the FVIII/vWF complex) wherein Willebrand factor serves both as transporter and protector of said factor VIII. As a matter of fact, the saline buffers of elution used are generally not capable of dissociating an antigen-antibody bond. Reciprocally, Applicants have noticed that the conventional buffers for dissociation of antigen and antibody bonds (acidic or chaotropic buffers) destroy the factor VIII procoagulant activity. D. N. Fass et al. nevertheless described such a buffer which is both able to dissociate an antigen-antibody bond and to preserve the procoagulant factor VIII activity. Such process was not used for fixation and elution of FVIII/vWF complex but rather of VIII:C already dissociated, and moreover, such a buffer (50% ethylene-glycol) requires, on an industrial scale, difficult steps for elimination of ethylene-glycol thereby resulting in significant product losses.

Consequently, it is proposed according to the invention:
  to supply a product for therapeutical use having not only the antihaemophilic A activity but also von Willebrand activity, contrary to the isolated FVIII:C which does not possess Willebrand activity and contrary to the concentrate, the Willebrand activity of which is insufficient;
  to supply, therefore, such a FVIII/vWF complex for therapeutical use having the above mentioned activity but having moreover a much higher purity than that of the cryoprecipitate and the concentrate;
  to supply, furthermore, such a FVIII/vWF complex of therapeutical use of high purity having a concentration of factor VIII higher than that of the cryoprecipitate and the concentrate;
  to supply thus a physiological molecule in which factor VIII, contrary to the isolated FVIII:C, is associated with Willebrand factor which serves as transporter and protector;
  to also supply a process for obtaining the FVIII/vWF complex having the above defined characteristics with a yield higher than that in the concentrate production, such process being moreover directly applicable to human plasma.

According to the invention, the process in question is based on the well known principle of immunopurification (Immunoadsorbents in protein purification (E. Ruoslahti Ed., Sc. J. Immunol. 1976 Supplement No 3, pages 1 to 84—Characterization of a monoclonal antibody to human interferon and its use in affinity chromatography, Stenman et al., J. and Immunol. Meth. (1981) 46 p. 337–345).

When its principle is applied in the particular case of factor VIII, it must be noted that the latter behaves in a very specific manner, i.e. it loses irreversibly its procoagulant activity in the elution solutions which are usually employed in immunopurification such as for example glycine hydrochloride, acetate buffer solution of low pH, KSCN and analogous conditions.

This invention however, proposes to respect both the procoagulant function of factor VIII and the integrity of the FVIII/wWF complex and its object is consequently a process characterized by including a fixation of the FVIII/vWF complex in physiological medium on a specific monoclonal antibody and releasing said complex by means of a suitable elution medium having no effect on the nature and the functions of such FVIII/vWF complex but able to dissociate the bonds linking the selected monoclonal antibody to the FVIII/vWF complex, thus collecting the latter in a highly purified form.

According to other characteristics:
the antibody is bound to a solid carrier;
the monoclonal antibody is selected among those to bind the FVIII/vWF complex in physiological medium and then to release such complex in the elution medium, the antibody itself not being denatured and recovering its capacity of fixing the FVIII/wWF complex after its return into the physiological medium thereby permitting repeated purification cycles;
preferably, the antibody responsive to the above definition is a monoclonal antibody derived from a hybridome selected after a series of hybridations of cells of mouse myelome X63 and mouse splenocytes BALB/C immunized with FVIII/vWF complex;
the elution medium is selected among the alkaline solution having a pH of between 8.5 and 10.5;
the alkaline solution is selected among the following bases: NaOH, NH$_4$OH, ethanolamine, diethanolamine, triethanolamine and the like.

According to particular mode of embodiment the selection is effected in three steps:

1. The antibodies anti-VIIIR:Ag are identified by means of von Willebrand factor (VIIIR:Ag) fixed on titration plate and of anti-mouse immunoglobulines goat antibody (marked by 125 iodine).
2. The antibodies anti-VIIIR:Ag identified as mentioned above are coupled to solid particles of the gel type and they are thereafter tested for their ability to bind the FVIII/vWF complex from plasma, resulting in the decrease of the antihaemophilic A and Willebrand activities tested in vitro.
3. The antibodies anti-VIIIR:Ag coupled with the solid particles and capable of fixing efficiently the FVIII/vWF complex are tested for their ability to release the FVIII/vWF complex in alkaline medium (pH 8.5 to 10.5); the eluted antihaemophilic A and von Willebrand activities are tested in vitro by the known processes.

According to other characteristics the collected FVIII/vWF complex can be concentrated by a known process of ultrafiltration or aminohexyl-Sepharose chromatography; the process can be completed with a gel filtration step and/or a lyophilization step.

The following example is given as an illustration and does not at all limit the present invention:

Splenocytes of BALB/c mouse hyperimmunized with complex FVIII/vWF were fused by means of polyethylene-glycol with cells of mouse myeloma (X63 cell line). The hybridomas producing antibodies anti-VIIIR:Ag are selected and the produced antibodies are coupled with solid particles of Sepharose 4B type and tested:
for their capacity of fixing FVIII/vWF complex;
among those which have given a positive result as to such capacity of fixing such complex, for their aptitude to release the FVIII/vWF complex in alkaline medium (pH 8.5 to 10.5), the antihaemophilic A and von Willebrand activities fixed in the above first test and eluted following the second test being tested in vitro by known processes.

The monoclonal antibody produced by the hybridoma selected as above is then placed in a suitable proteic medium and coupled with Sepharose 4B (dextrane polymer). A column of 1 liter is then filled with gel coupled with the antibody.

The column equilibrated with sodium chloride 0.1M is loaded with 10 liters of plasma at a flow rate of 0.5 liter per hour. The column is then washed with 2 liters of sodium chloride 0.1M, then eluted with 2 liters of triethanolamine, 100 mM (pH 9.9). The whole of the active product is collected in 1 liter of eluent and contains about 5000 I.U. of factor VIII and of Willebrand factor, i.e. a yield of 50% and a concentration of 5 I.U. per ml. This product contains 100 times less contaminants than the cryoprecipitate and 10 times less than its concentrate.

Its specific activity reaches 20 I.U./mg both in VIII procoagulant activity and von Willebrand activity.

As the proteic contents is very low (100 times less than in the cryoprecipitate), the product can be concentrated up to 25 times (125 I.U. per ml) either by ultrafiltration or by aminohexyl-Sepharose chromatography. The use of triethanolamine as an elution buffer allows direct lyophilization of the eluted product. This facility also exists if other volatile bases (NH$_4$OH, ethanolamine, diethanolamine or analogous compounds) are used.

The column reequilibrated with sodium chloride 0.1M could be used again as described above with the same results.

When Sephacryl (dextrane and acrylamide polymer) was used in the above described operations instead of Sepharose, concentrations of 16 I.U. per ml were obtained. Similarly, other analogous gels can be used such as Trisacryl (tris- and acrylamide polymer).

The product resulting from the process is particularly suited to restore deficient activities in haemophilia A and von Willebrand patients through intravenous injection of small volume (500 I.U. in 4 ml).

It will be understood that this invention was only described in a purely explanatory and not at all limitative manner and that any useful modification can be made therein by substituting equivalents without however departing from its scope. Thus, the process according to this invention can be particularly applied to purification of FVIII/vWF complex from cryoprecipitate or any other medium containing it.

We claim:

1. A process to produce FVIII/vWF complexes for therapeutical use possessing both haemophilic A activity and von Willebrand activity as well as a high degree of purity, such process substantially comprising the steps of:
   fixing the FVIII/vWF complex in physiological medium on a monoclonal antibody able to release such complex between pH 8.5 and 10.5; and
   releasing said complex by means of an elution medium of pH 8.5–10.5 having no effect on the functions of the FVIII/vWF complex but able to dissociate bonds between said monoclonal antibody and the FVIII/vWF complex;
   then collecting the FVIII/vWF complex in a purified form.

2. A process according to claim 1, wherein the antibody is linked to a solid carrier.

3. A process according to claim 1, wherein the same monoclonal antibody is used in several cycles.

4. A process according to claim 1, wherein the monoclonal antibody is derived from a hybridoma selected after a series of hybridations of mouse X63 myeloma cells and splenocytes of BALB/c mouse immunized with FVIII/vWF complex.

5. A process according to claim 1, wherein the bases entering into the composition of the elution medium are of the volatile type selected among the group comprising $NH_4OH$, ethanolamine, diethanolamine, and triethanolamine.

6. A process according to claim 1, wherein the immunopurified FVIII/vWF complex is submitted to a lyophilization step.

7. A process according to claim 1, further comprising the step of concentrating said collected complex by ultrafiltration or aminohexyl-Sepharose chromatography.

8. A process according to claim 1, further comprising the step of gel-filtering said collected complex.

9. As a novel industrial product, a monoclonal anti-VIIIR:Ag antibody bound to a solid carrier, such monoclonal antibody being derived from a hybridoma selected after a series of hybridations of mouse X63 myeloma cells and splenocytes from BALB/c mouse immunized with the FVIII/vWF complex.

10. A monoclonal anti-VIIIR:Ag antibody according to claim 9, wherein said solid carrier is a gel.

11. A monoclonal anti-VIIIR:Ag antibody according to claim 9, in a proteic envisonment.

12. A product of therapeutical use having not only the antihemophilic A activity but also the von Willebrand activity consisting of a FVIII/vWF complex of high purity with a specific activity of about 20 I.U./mg for both VIII procoagulant activity and von Willebrand activity.

* * * * *